US012678343B2

(12) United States Patent　　　(10) Patent No.:　US 12,678,343 B2
Sablone　　　　　　　　　　　　　(45) Date of Patent:　　　Jul. 14, 2026

(54) ABSORBENT SANITARY ARTICLE AND METHOD FOR ITS PRODUCTION

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 406 days.

(21) Appl. No.: 18/336,119

(22) Filed: Jun. 16, 2023

(65) Prior Publication Data

US 2023/0404819 A1　　　Dec. 21, 2023

(30) Foreign Application Priority Data

Jun. 20, 2022　　(IT) ........................ 102022000013009

(51) Int. Cl.
| | |
|---|---|
| *A61F 13/496* | (2006.01) |
| *A61F 13/15* | (2006.01) |
| *A61F 13/49* | (2006.01) |
| *A61F 13/494* | (2006.01) |
| *A61F 13/495* | (2006.01) |

(52) U.S. Cl.
CPC ...... *A61F 13/496* (2013.01); *A61F 13/15577* (2013.01); *A61F 13/49012* (2013.01); *A61F 13/49466* (2013.01); *A61F 13/495* (2013.01)

(58) Field of Classification Search
CPC .............. A61F 13/496; A61F 13/15577; A61F 13/49012; A61F 13/49466; A61F 13/495; A61F 13/49473; A61F 2013/49493
See application file for complete search history.

(56) References Cited

U.S. PATENT DOCUMENTS

| | | | |
|---|---|---|---|
| 11,096,836 B2 | 8/2021 | Bishop et al. | |
| 2003/0050616 A1* | 3/2003 | Reynolds .......... | A61F 13/49466 604/369 |
| 2018/0071155 A1* | 3/2018 | Bishop ................ | A61F 13/4942 |

FOREIGN PATENT DOCUMENTS

AU　　　　2017412281 A1　11/2019

OTHER PUBLICATIONS

Search Report dated Feb. 3, 2023. 7 pages.

* cited by examiner

*Primary Examiner* — Rebecca E Eisenberg
*Assistant Examiner* — Timothy L Flynn
(74) *Attorney, Agent, or Firm* — RMCK Law Group PLC

(57) ABSTRACT

An absorbent sanitary article includes a chassis, a pair of elastic side panels, and a gasketing element having an outer transverse edge attached to the chassis and side edges attached to respective side panels.

15 Claims, 5 Drawing Sheets

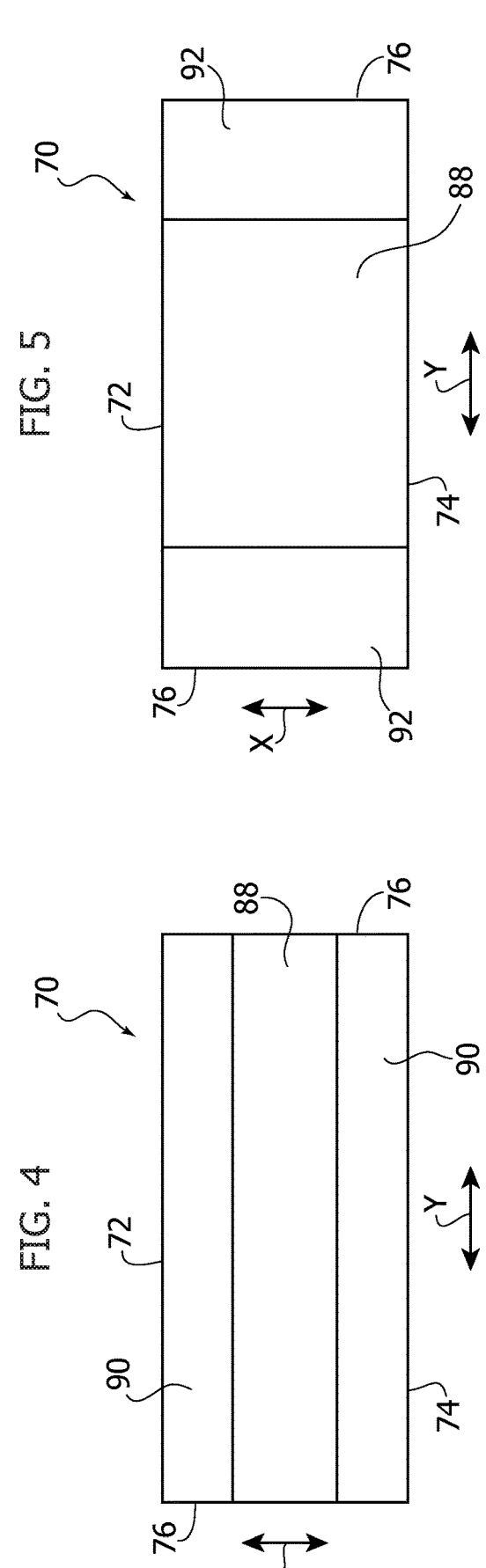
FIG. 4
FIG. 5
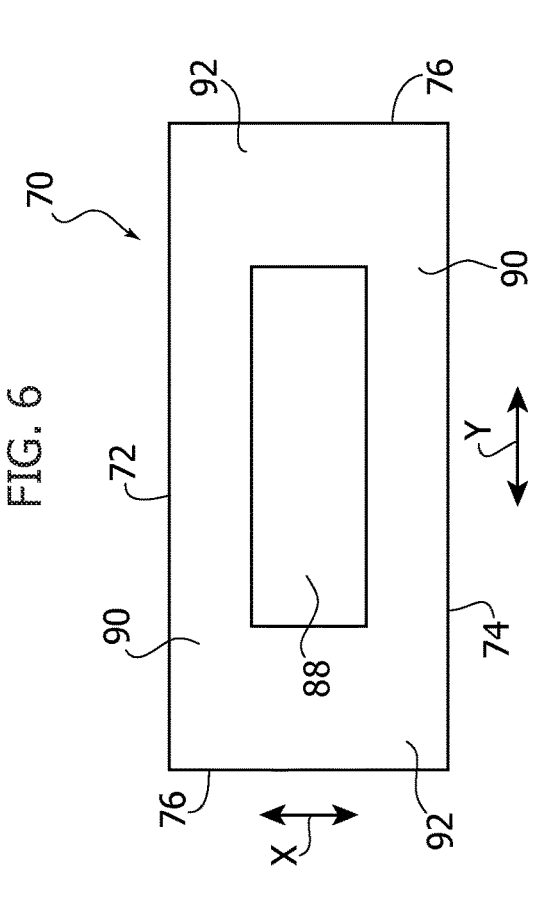
FIG. 6

ABSORBENT SANITARY ARTICLE AND METHOD FOR ITS PRODUCTION

CROSS-REFERENCE TO RELATED APPLICATION

This application claims priority to Italian Patent Application No. 102022000013009 filed Jun. 20, 2022. The disclosure of the above application is incorporated herein by reference in its entirety.

FIELD OF THE INVENTION

The present invention relates to absorbent sanitary articles such as, for example, diapers, diaper-pants, incontinence pads for incontinent adults, etc.

The present invention also relates to a method for producing absorbent sanitary articles.

BACKGROUND OF THE INVENTION

Absorbent sanitary articles typically have a central body or chassis having a rear section, a front section and a crotch section extending between the rear section and the front section, and which extends between the user's legs in the condition in which the absorbent sanitary article is worn. The chassis normally comprises a topsheet of liquid-permeable material intended to come into contact with the user's skin when the article is worn, a backsheet of impermeable material and an absorbent core sandwiched between the topsheet and the backsheet. The rear section and front section of the chassis are normally closed around the waist of the user by at least one pair of side panels which project laterally beyond the side edges of the chassis. The side panels may be elastically extensible in the transverse direction.

One of the most common problems with absorbent sanitary articles is the possibility that body exudates may leak from the rear or front waist section of the absorbent article. The risk of leakage is higher in the case of semi-solid fecal material that is not absorbed by the absorbent core and that may leak from the space between the waistband of the absorbent sanitary article and the user's skin.

Various solutions have already been proposed in the state of the art, which tend to limit the risk of leakage of solid or semi-solid body exudates from the front or rear waist sections of an absorbent sanitary article. One such solution is described in US 2020/0038256 A1. This document discloses an absorbent sanitary article including a chassis and at least one gasketing element applied to the topsheet and having an outer transverse edge attached to the topsheet and an inner transverse edge detached from the topsheet so that, during use, it forms a pocket facing the crotch section of the chassis that may receive and contain solid or semi-solid exudates.

The known solutions that envisage the use of a gasketing element as described in US 2020/0038256 A1 do not work correctly if the gasketing element remains adherent to the surface of the topsheet in the condition in which the absorbent sanitary article is worn. Indeed, in this case the pocket formed between the gasketing element and the topsheet remains closed, and the gasketing element is not in a condition to receive and contain solid or semi-solid exudates.

The known solutions often have problems in ensuring the correct detachment of the inner transverse edge of the gasketing element from the surface of the topsheet in the condition wherein the absorbent sanitary article is worn.

OBJECT AND SUMMARY OF THE INVENTION

The object of the present invention is to provide an absorbent sanitary article that solves the problems of the prior art.

In particular, the object of the present invention is to provide an absorbent sanitary article provided with at least one gasketing element capable of forming a pocket for receiving solid or semi-solid exudates which, in the condition wherein the absorbent sanitary article is worn is open and in the best condition to receive such exudates.

According to the present invention, this object is achieved by an absorbent sanitary article having the characteristics forming the subject of claim 1.

According to another aspect, the invention relates to a method for producing absorbent sanitary articles having the characteristics forming the subject of claim 10.

Preferred embodiments of the invention form the subject of the dependent claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

It will be appreciated that the accompanying drawings are schematic and that—in certain figures—some components may not be shown to assist in understanding the Figures. It will be appreciated that the various figures may also not be represented on the same scale.

DETAILED DESCRIPTION

Figure 1:
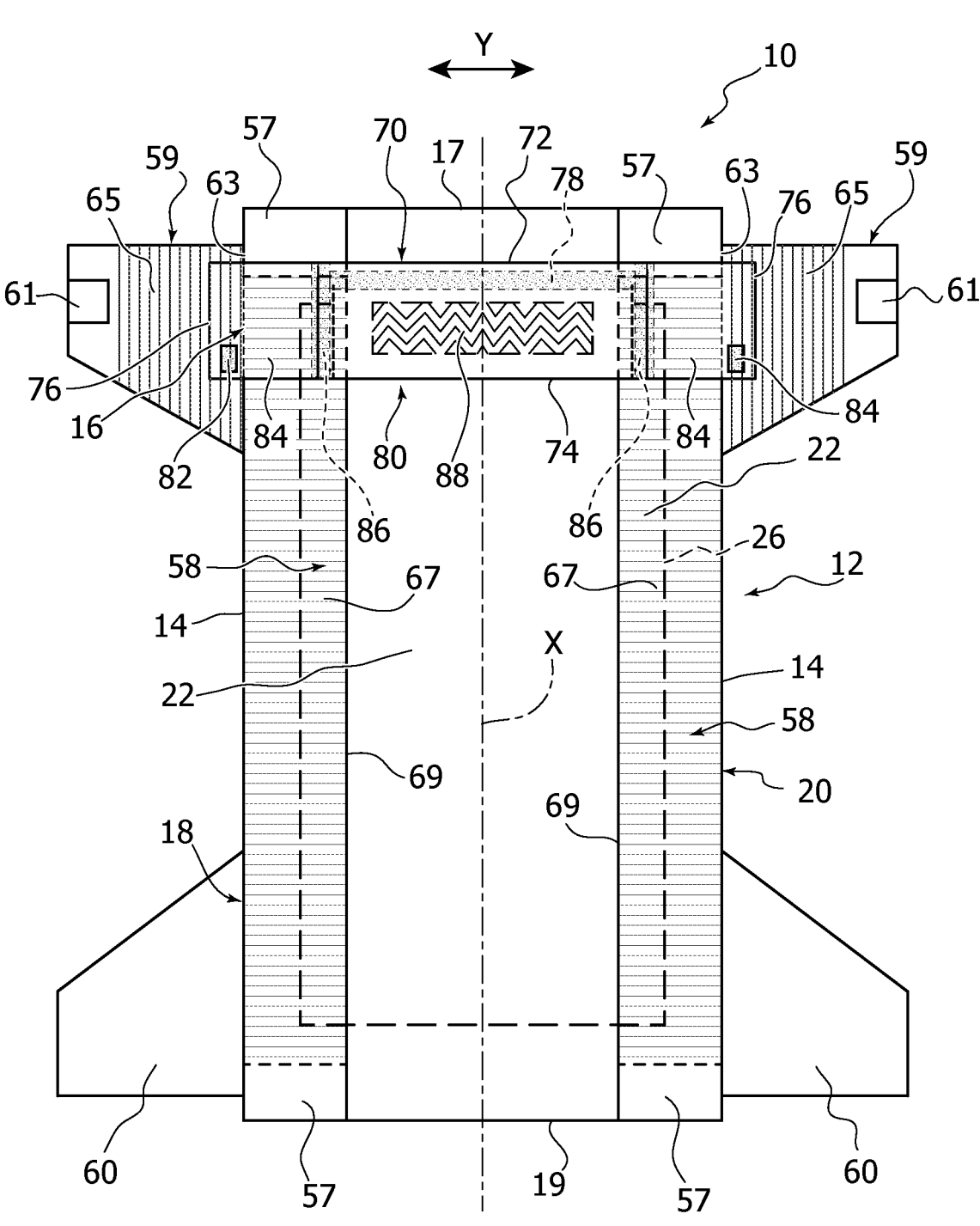
FIG. 1 is a plan view of an absorbent sanitary article according to an embodiment, in an extended position.
Figure 2:
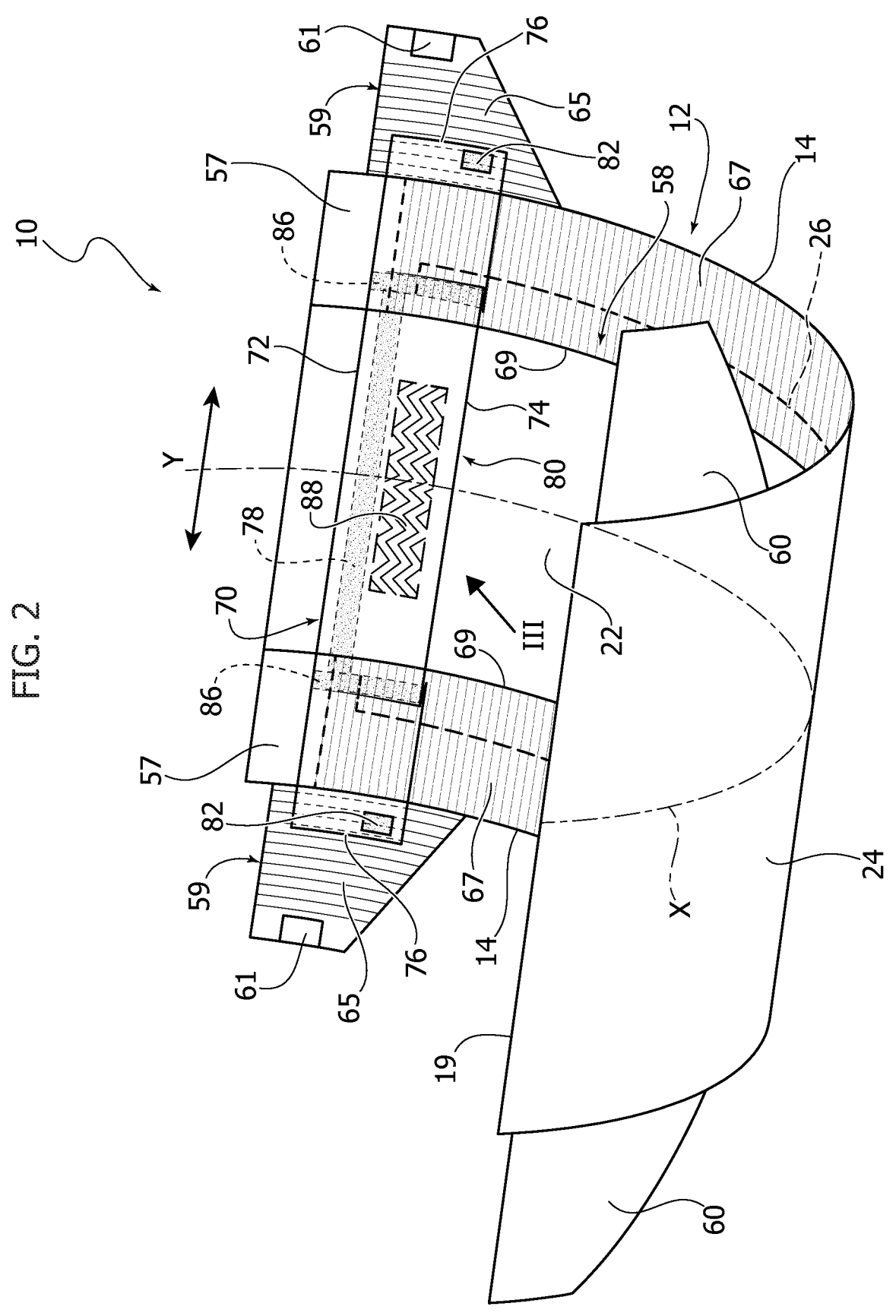
FIG. 2 is a schematic perspective view showing the absorbent sanitary article of FIG. 1 in a configuration of use.
Figure 3:
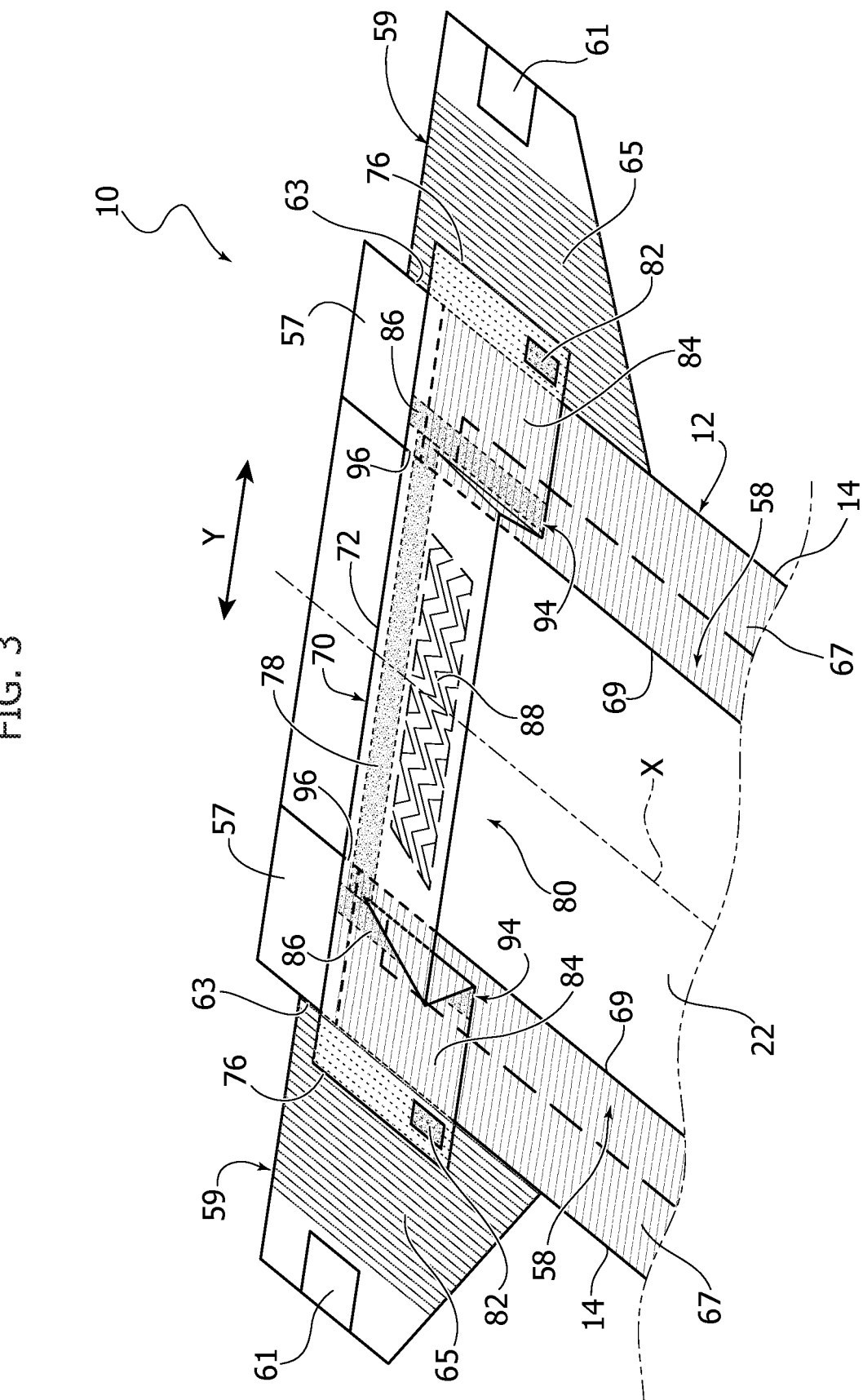
FIG. 3 is a perspective view on a larger scale of the part indicated by the arrow III in FIG. 2, FIGS. 4, 5 and 6 are plan views of possible embodiments of a gasketing element indicated by the arrow IV in FIG. 3.

With reference to FIGS. 1-3, numeral 10 indicates an absorbent sanitary article according to the present invention. FIG. 1 shows the absorbent sanitary article in an extended configuration and FIG. 2 shows the absorbent sanitary article 10 in a configuration in which it is about to be worn.

The absorbent sanitary article 10 comprises a chassis 12 extended along a longitudinal axis X. The chassis 12 has two side edges 14 and two transverse edges 17, 19, which extend along a transverse direction Y perpendicular to the longitudinal axis X.

The chassis 12 has a rear waist section 16, a front waist section 18 and a crotch section 20, which extends between the rear waist section 16 and the front waist section 18. In a configuration of use, the rear and front waist sections 16, 18 are closed around the waist of the user, and the crotch section 20 extends between the legs of the user. The rear and front waist sections 16, 18 may be non-elastic, i.e. lacking the possibility of elastically extending in the transverse direction Y.

The chassis 12 may have a rectangular shape as illustrated in FIG. 3, in which the two side edges 14 are straight and parallel to the longitudinal axis X. In a possible embodiment, the side edges 14 may be curved and shaped so as to conform to the user's legs in the configuration wherein the absorbent sanitary article 10 is worn. In this case, the chassis 12 may have substantially an hourglass shape.

The chassis 12 comprises a topsheet 22 constituted by a sheet of liquid-permeable material and having an outer surface which—during use—is in contact with the user's skin. The chassis 12 also comprises an impermeable back-sheet 24 (FIG. 2) and an absorbent core 26 which is sandwiched between the topsheet 22 and the backsheet 24.

With reference to FIGS. 1-3, the absorbent sanitary article 10 comprises at least one pair of side panels 59, extending laterally outwards from respective side edges 14 of the chassis 12 in at least one of the rear and/or front waist sections 16, 18. In the embodiment illustrated in the figures, the absorbent sanitary article 10 comprises a pair of rear side panels 59 extending laterally outwards from the rear waist section 16 and a pair of front side panels 60 extending laterally outwards from the front waist section 18.

Closure formations 61, for example micro-hook closure formations, may be attached to the distal ends of at least one pair of side panels, in the example illustrated to the pair of rear side panels 59. The front side panels 60 may have an outer surface of micro-loop material (e.g. a non-woven fabric) to establish a surface connection with the micro-hook closure formations 61 of the rear side panels 59. In the case in which the absorbent sanitary article 10 has only one pair of side panels (usually a pair of rear side panels) the waist section opposite to the one carrying the pair of side panels may have a micro-loop panel on its outer surface for establishing surface closure with the micro-hook closure formations 61.

The side panels 59, 60 have respective proximal edges 63 attached along respective side edges 14 of the chassis 12 at the rear waist section 16 or at the front waist section 18. At least one pair of side panels 59, 60 has an elastic portion 65 that can be elastically extended along the transversal direction Y.

In the example illustrated in the figures, the rear side panels 59 are elastic and the front side panels 60 may be non-elastic. The rear side panels 59 may comprise elastic elements such as elastic threads or films sandwiched between two non-woven webs. The front side panels 60 may be formed from one or more non-woven layers. In a possible embodiment, both the rear side panels 59 and the front side panels 60 may have respective elastic portions 65.

The absorbent sanitary article 10 may comprise two leg cuffs 58. The two leg cuffs 58 may be formed by respective strips elongated in the direction of the longitudinal axis X and located along respective side edges 14 of the chassis 12. The leg cuffs 58 have respective outer edges attached to the chassis 12 and respective inner edges 69 detached from the inner surface of the topsheet 22 and elastically tensioned, so that the inner edges 69 of the leg cuffs 58 in the configuration of use are elastically held in contact with the user's legs, and form barriers that help to reduce the leakage of liquid, solid or semi-solid bodily exudates in the crotch section 20 of the chassis 12.

The leg cuffs 58 may be configured in various ways. In one possible embodiment, the leg cuffs 58 may be formed separately from the topsheet 22 and may comprise a plurality of elastic threads arranged between two non-woven layers. The elastic threads may be anchored to the two non-woven layers in discrete points, for example, by glue dots or by anchor welding, for example, as described in EP 3092997 and U.S. Pat. No. 6,291,039. Between the discrete anchor points spaced apart in the longitudinal direction the elastic threads are free to contract so that the two non-woven layers assume a pleated shape when the elastic threads are at rest.

The leg cuffs 58 may also be formed by folding side portions of the topsheet 22 inwards, i.e. towards the longitudinal axis X, so as to enclose the elastic threads tensioned in the longitudinal direction between two layers of topsheet superimposed on each other. In another example, the leg cuffs 58 may be formed by applying additional non-woven strips to the topsheet 22 at the side edges 14 of the chassis 12 so as to enclose elastic threads tensioned in the longitudinal direction between the topsheet and the additional non-woven strips.

The elastic leg cuffs 58 generally have end portions 57 in which the inner edge 69 of the leg cuffs 58 is also attached to the topsheet 22. The leg cuffs 58 have respective central portions 67 comprised between the end portions 57 in which the respective inner edges 69 are detached from the topsheet 22. The end portions 57 of the leg cuffs 58 are not elastically extensible while the inner edges of the central portions 67 are elastically extensible in the longitudinal direction X.

With reference to FIGS. 1-3, the absorbent sanitary article 10 comprises at least one gasketing element 70 applied to the outer surface of the topsheet 22 in at least one of the rear and front waist sections 16, 18. In the embodiment illustrated by way of example in the figures, the absorbent sanitary article 10 comprises a single gasketing element 70 located in the rear waist section 16. In possible embodiments, the absorbent sanitary article 10 could comprise a rear gasketing element located in the rear waist section 16 and a front gasketing element located in the front waist section 18.

The gasketing element 70 is a separate component with respect to the topsheet 22 and with respect to the side panels 59. The gasketing element 70 may have the shape of a rectangular strip elongated in the transverse direction Y. The gasketing element 70 may have an elastic portion that can be stretched elastically in the transverse direction Y or it can be made of non-elastic material (for example, from one or more non-woven layers).

The gasketing element 70 comprises an outer transverse edge 72, an inner transverse edge 74 and two side edges 76. In a possible embodiment, the outer transverse edge 72 of the gasketing element 70 is attached to the topsheet 22 along a continuous transverse attachment line 78 and is attached to the leg cuffs 58 along longitudinal attachment lines 86. The attachment lines 78 and 86 form an attachment area having a substantially C shape facing the crotch section 20 of the chassis 12.

The inner transverse edge 74 is detached from the outer surface of the topsheet 22 so as to form a pocket 80 open towards the crotch section 20 of the chassis 12. The pocket 80 is closed on three sides by the attachment lines 78, 86. The attachment lines 78, 86 may be made by glue or welding (thermal or ultrasonic). In a possible embodiment, the attachment lines 86 between the gasketing element 70 and the leg cuffs 58 extend over portions of the leg cuffs 58 that are detached from the topsheet 22.

At least one of the side edges 76 of the gasketing element 70 extends in the transverse direction beyond the respective side edge 14 of the chassis 12 and is attached to a respective elastic portion 65 of a respective side panel 59.

At least part of the elastic portion 65 of a respective side panel 59 is arranged between the side edge 76 of the gasketing element 70 and the proximal edge 63 of the respective side panel 59.

In the embodiment shown in FIGS. 1-3, both side edges 76 of the gasketing element 70 extend in the transverse direction Y beyond the respective side edges 14 of the chassis 12, and are attached to respective elastic portions 65 of the respective side panels 59. The attachment areas between the side edges 76 of the gasketing element 70 and the elastic portions 65 of the side panels 59 are indicated by 82. This attachment may be done by glue or welding (thermal or ultrasonic). The attachment areas 82 may be adjacent to the inner edge 74 of the gasketing element 70 and may extend in the direction of the X axis only for a small part of the length of the side edges 76.

In a possible embodiment, discontinuity regions 84 are arranged between the attachment areas 82 in which the gasketing element 70 is attached to the side panels 59 and the attachment areas 78, 86 in which the gasketing element 70 is fixed to the chassis 12, so that in these discontinuity regions 84 the gasketing element 70 is detached from the chassis 12 and from the side panels 59.

In a possible embodiment, the gasketing element 70 may consist of a single layer of an elastic film.

In a possible embodiment, the gasketing element 70 may consist of an elastic composite material.

In a possible embodiment, the gasketing element 70 may be formed of an elastic laminate including an elastic film sandwiched between two non-woven layers anchored to each other and to the elastic film by means of a pattern of connecting points formed by glue or welding (thermal or ultrasonic).

In a possible embodiment, the gasketing element 70 may comprise a plurality of elastic threads or a plurality of elastic tapes sandwiched between two non-woven layers anchored to each other and to the elastic threads or elastic tapes by a pattern of connecting points formed by glue or welding (thermal or ultrasonic).

With reference to FIG. 4, in a possible embodiment, the gasketing element 70 may comprise an elastic element 88 having a smaller dimension than the gasketing element 70 in the longitudinal direction X, and the same dimension as the gasketing element 70 in the transverse direction Y, so that the gasketing element 70 has two non-elastic transverse portions 90 located on opposite sides of the elastic element 88.

With reference to FIG. 5, in a possible embodiment, the gasketing element 70 may comprise an elastic element 88 having a smaller dimension than the gasketing element 70 in the transverse direction Y and the same length as the gasketing element 70 in the longitudinal direction X, so that the gasketing element 70 has two non-elastic longitudinal portions 92 located on opposite sides of the elastic element 88.

With reference to FIG. 6, in a possible embodiment, the elastic element 88 may have a smaller size than the gasketing element 70 both in the longitudinal direction X and in the transversal direction Y, so that the gasketing element 70 has two non-elastic transverse portions 90 and two non-elastic longitudinal portions 92 forming a non-elastic frame that surrounds the elastic element 88.

In a possible embodiment, the gasketing element 70 may consist of a non-elastic element. For example, the gasketing element 70 could consist of one or more non-woven layers.

Both when the gasketing element 70 is elastically extensible in the transverse direction Y and when the gasketing element 70 is not elastically extensible, the gasketing element 70 may have at least one fold 94 (FIG. 3) parallel to the longitudinal axis X. In a possible embodiment, the gasketing element 70 may have two longitudinal folds 94, each having an S or Z shape, so that the gasketing element 70 is folded according to a general Ω configuration. The longitudinal folds 94 may be located inside the attachment lines 86 that attach the gasketing element 70 to the leg cuffs 58. The edges of the folds 94 may be attached together by welding points 96 adjacent to the outer transverse edge 72 of the gasketing element 70.

When the absorbent sanitary article 10 is worn, the rear side panels 59 are elastically stretched in the transverse direction Y before connecting the micro-hook closure formations 61 with micro-loop surfaces provided on the front side panels 60 or on a front panel applied to the outer surface of the front waist section 18. During the elastic stretching in the transverse direction of the side panels 59, the inner transverse edge 74 of the gasketing element 70 is pulled in the transverse direction Y. The extension in the transverse direction Y of the inner transverse edge 74 of the gasketing element 70 is made possible by the elasticity in the transverse direction of the gasketing element 70 or the opening of the folds 94, or a combination thereof. The extension in the transverse direction of the inner transverse edge 74 of the gasketing element 70 causes the detachment of the inner transverse edge 74 from the topsheet 22 and the opening of the pocket 80 along the inner transverse edge 74. This ensures that when the absorbent sanitary article 10 is worn the pocket 80 formed between the gasketing element 70 and the topsheet 22 is open and is in the best conditions for receiving and containing solid or semi-solid bodily exudates remaining between the skin of the user and the topsheet 22.

During the transverse stretching of the elastic panels 59, the gasketing element 70, being attached to the portions 67 of the leg cuffs 58 detached from the topsheet 22, lifts the inner edges 69 of the leg cuffs 58, thus forming a containment volume between the topsheet 22, the leg cuffs 58 and the gasketing element 70, which is effective in receiving and retaining solid and semi-solid bodily exudates.

As indicated above, the absorbent sanitary article 10 may have a single gasketing element 70 located in only one of the waist sections (for example, the rear waist section 16, which is the one most exposed to receiving solid or semi-solid bodily exudates) or it may comprise two gasketing elements 70, each configured as previously described and located, respectively, in the rear waist section 16 and in the front waist section 18.

Figure 7:
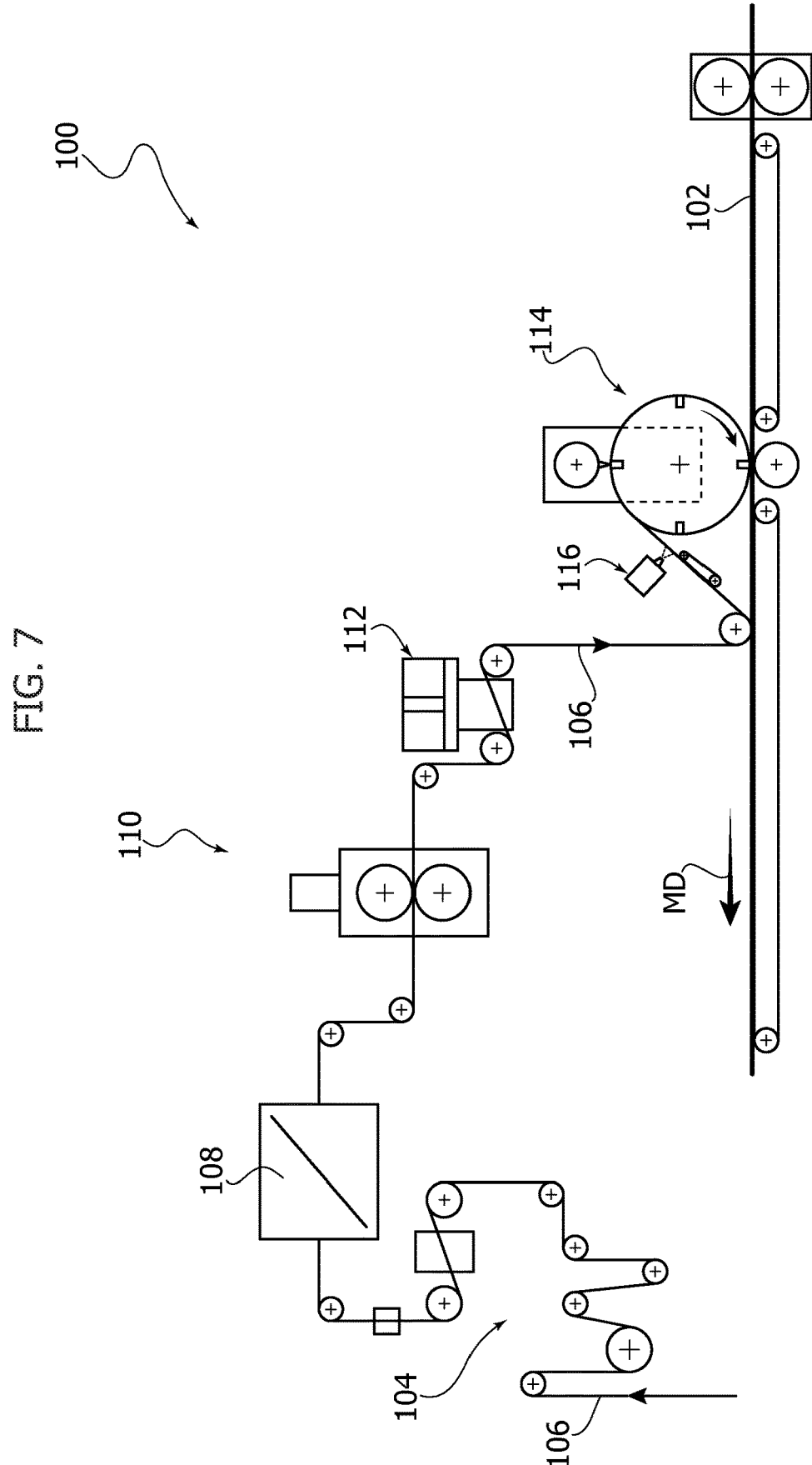
FIG. 7 is a schematic side view of an embodiment of a machine for producing absorbent sanitary articles according to the present invention.

With reference to FIG. 7, numeral 100 schematically indicates an apparatus for producing absorbent sanitary articles according to the present invention.

A continuous chassis chain 102 travels in the machine direction MD. The continuous chassis chain 102 may be in the form of a continuous composite web or may be formed of discrete elements. The continuous chassis chain 102 may be produced with apparatuses known in the sector for producing absorbent sanitary articles. On the continuous chassis chain 102, elastic side panels 59 and, possibly, are applied at regular intervals by techniques known per se in the sector.

The apparatus 100 comprises a feed unit 104, which feeds a continuous sheet 106. The continuous sheet 106 may be an elastic laminate that is elastically extensible in the transverse direction, or it may be a non-elastic sheet. The apparatus 100 may comprise a folding device 108 configured for forming continuous longitudinal folds on the continuous sheet 106 parallel to the direction of movement. Downstream of the folding device 108, a welding device 110 may be provided, configured to carry out weldings between the folded edges of the continuous sheet 106 at predetermined positions and spaced apart from each other in the longitudinal direction. An edge alignment device 112 may be provided downstream of the welding device 110.

The apparatus 100 comprises a cut-and-slip unit 114 configured to transversely cut the sheet 106 to form individual gasketing elements 70, which are applied with a predetermined phase relationship onto the continuous chassis chain 102 as it advances in the machine direction MD. Upstream of the cut-and-slip unit 114, a glue applicator device 116 may be arranged, which is configured to apply glue patterns onto the continuous sheet 106 with a predetermined phase relationship. The glue applied by the glue applicator device 116 serves to attach the gasketing elements 70 onto the continuous chassis chain 102 along the attachment areas 78, 82, 86, as previously described. Alternatively, instead of the glue applicator device 116, a welding device could be provided located downstream of the cut-and-slip unit 114 and configured to weld the individual gasketing elements 70 onto the continuous chassis chain 102 so as to produce—by welding—the previously described attachment areas 78, 86, 82.

When the continuous chassis chain 102 is made in the form of a continuous composite web, after attachment of the gasketing element, the continuous composite web is transversely cut to form individual absorbent sanitary articles 10.

In a possible embodiment, the method may envisage attachment of the individual gasketing elements 70 (by glue or welding) onto a continuous backsheet and, subsequently, the application and attachment of the continuous topsheet onto the continuous chassis chain 102.

The apparatus 100 implements a method comprising:

forming a continuous chassis chain 102 and a plurality of pairs of side panels 59, 60 applied at regular intervals on the continuous chassis chain 102, providing a continuous sheet 106 movable in the direction of its longitudinal axis and transversally cutting said continuous sheet 106 so as to form a plurality of gasketing elements 70, spacing apart the gasketing elements 70 in the longitudinal direction and attaching the gasketing elements 70 to the continuous chassis chain 102 so that the transverse outer edges 72 of the gasketing element 70 are attached to the continuous chassis chain 102 and the outer edges 76 of the gasketing elements 70 are attached to elastic portions 65 of the side panels 59, 60.

Of course, without prejudice to the principle of the invention, the details of construction and the embodiments may be widely varied with respect to those described and illustrated, without thereby departing from the scope of the invention as defined by the claims that follow.

The invention claimed is:

1. An absorbent sanitary article, comprising: a chassis having a longitudinal axis, two side edges, a rear waist section, a front waist section and a crotch section intermediate between the rear waist section and the front waist section, wherein the chassis comprises a topsheet having an outer surface which, during use, faces the user's body, a backsheet and an absorbent core interposed between the topsheet and the backsheet, at least one pair of side panels extending laterally outwards from the respective side edges of the chassis in at least one of the rear and front waist sections, wherein said at least one pair of side panels have respective proximal edges fixed to the chassis and respective elastic portions elastically extendable along a transverse direction perpendicular to said longitudinal axis, and at least one gasketing element applied to the outer surface of the topsheet in at least one of said rear and front waist sections, wherein:

said at least one gasketing element has an outer transverse edge, an inner transverse edge and two side edges, the outer transverse edge is attached to the chassis and the inner transverse edge is detached from the outer surface of the topsheet to form a pocket open towards said crotch section, and at least one of said side edges of the at least one gasketing element extends in a transverse direction beyond the respective side edge of the chassis, and is fixed to a respective side panel of the at least one pair of side panels, and wherein at least part of the respective elastic portion of the at least one pair of side panels is arranged between said side edge of the gasketing element and said proximal edge of said respective side panel.

2. The absorbent sanitary article of claim 1, wherein both side edges of the at least one gasketing element extend in the transverse direction beyond the respective side edges of the chassis and are fixed to respective elastic portions of the respective side panels.

3. The absorbent sanitary article of claim 1, comprising at least one discontinuity region arranged between attachment areas of the at least one gasketing element to a respective side panel and to the chassis, wherein in said at least one discontinuity region, said at least one gasketing element is detached from the chassis.

4. The absorbent sanitary article of claim 1, comprising a pair of leg cuffs extending on the topsheet parallel to said longitudinal axis, wherein said at least one gasketing element is fixed to the topsheet and to said pair of leg cuffs.

5. The absorbent sanitary article of claim 1, wherein said at least one gasketing element comprises an elastic element elastically stretchable in said transverse direction.

6. The absorbent sanitary article of claim 1, wherein said at least one gasketing element is not elastically stretchable.

7. The absorbent sanitary article of claim 1, wherein said at least one gasketing element comprises longitudinal folds which extend parallel to said longitudinal axis.

8. The absorbent sanitary article of claim 7, wherein said at least one gasketing element is folded according to a general Q configuration.

9. The absorbent sanitary article of claim 1, further comprising a pair of leg cuffs, wherein said at least one gasketing element is attached to the topsheet along a continuous transverse attachment line, and is attached to said pair of leg cuffs along attachment lines parallel to said longitudinal axis, wherein said at least one gasketing element is fixed to portions of said pair of leg cuffs detached from the topsheet.

10. The absorbent sanitary article of claim 1, wherein said at least one gasketing element is attached to the chassis along a continuous transverse attachment line along the outer transverse edge, the continuous transverse attachment line forming a closed side of the pocket opposite to an open side of the pocket that is open towards the crotch section, the continuous transverse attachment line having opposed transverse edges facing the respective proximal edges of the at least one pair of side panels; and wherein at least one discontinuity region is arranged at least along the transverse direction between an attachment area fixing the at least one gasketing element to said respective side panel and a respective transverse edge of the continuous transverse attachment line, wherein in said at least one discontinuity region, said at least one gasketing element is detached from the chassis.

11. The absorbent sanitary article of claim 1, comprising a pair of leg cuffs extending on the topsheet parallel to said longitudinal axis;

wherein said at least one gasketing element is attached to the topsheet along a continuous transverse attachment line along the outer transverse edge, the continuous transverse attachment line forming a closed side of the pocket opposite to an open side of the pocket that is open towards the crotch section, the continuous transverse attachment line having opposed transverse edges facing the respective proximal edges of the at least one pair of side panels;

wherein said at least one gasketing element is attached to said pair of leg cuffs along longitudinal attachment lines extending parallel to said longitudinal axis and positioned proximate respective opposed transverse edges of the continuous transverse attachment line so as to form a C-shaped pocket, wherein said at least one gasketing element is fixed to portions of said pair of leg cuffs that are detached from the topsheet.

12. The absorbent sanitary article of claim 11, comprising at least one discontinuity region arranged at least along the transverse direction between an attachment area fixing the at least one gasketing element to said respective side panel and a respective longitudinal attachment line, wherein in said at least one discontinuity region, said at least one gasketing element is detached from the chassis.

13. The absorbent sanitary article of claim 11, wherein said at least one gasketing element comprises two longitudinal folds which extend parallel to said longitudinal axis, wherein respective longitudinal folds are positioned adjacent respective longitudinal attachment lines on an inner side thereof opposite an outer side of the longitudinal attachment lines facing the respective proximal edges of the at least one pair of side panels.

14. The absorbent sanitary article of claim 1, where the at least one gasketing element includes:

a length in the longitudinal direction between the inner and outer transverse edges, and a corner formed at each intersection of the inner transverse edge and a respective side edge of the two side edges, wherein the at least one of the side edges of the at least one gasketing element is fixed to the respective side panel via an attachment area at a respective corner of the at least one gasketing element, and wherein the attachment area extends in the longitudinal direction for only a small portion of the length in the longitudinal direction, the small portion being less than one-half the length in the longitudinal direction such that the respective side edge proximate the outer transverse line of the at least one gasketing element is detached from the respective side panel and the chassis.

15. A method for producing absorbent sanitary articles, comprising:

forming a continuous chassis chain and a plurality of pairs of side panels applied at regular intervals onto said continuous chassis chain, providing a continuous sheet movable in a direction of its longitudinal axis and transversely cutting said continuous sheet to form a plurality of gasketing elements, and spacing apart said plurality of gasketing elements from each other in the longitudinal direction and attaching said plurality of gasketing elements to said continuous chassis chain so that outer transverse edges of said plurality of gasketing element are attached to said continuous chassis chain and side edges of said plurality of gasketing elements are attached to elastic portions of said plurality of pairs of side panels.

* * * * *